United States Patent
Harada et al.

(10) Patent No.: US 8,314,411 B2
(45) Date of Patent: Nov. 20, 2012

(54) PARTICLE BEAM THERAPY SYSTEM

(75) Inventors: Hisashi Harada, Tokyo (JP); Takaaki Iwata, Tokyo (JP); Taizo Honda, Tokyo (JP); Yuehu Pu, Tokyo (JP); Yuichi Yamamoto, Tokyo (JP); Toshihiro Otani, Tokyo (JP); Hidenobu Sakamoto, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 236 days.

(21) Appl. No.: 12/738,705

(22) PCT Filed: Apr. 24, 2009

(86) PCT No.: PCT/JP2009/058166
§ 371 (c)(1),
(2), (4) Date: Apr. 19, 2010

(87) PCT Pub. No.: WO2010/122662
PCT Pub. Date: Oct. 28, 2010

(65) Prior Publication Data
US 2011/0218429 A1    Sep. 8, 2011

(51) Int. Cl.
*A61N 5/10* (2006.01)
*H01J 37/256* (2006.01)

(52) U.S. Cl. .......... 250/505.1; 250/396 ML; 250/396 R; 250/397; 250/492.3; 378/66; 378/19; 315/500; 315/111.61; 335/210

(58) Field of Classification Search ............... 250/505.1, 250/396 R, 396 ML, 397, 492.3; 315/500, 315/111.61; 378/66, 19; 335/210
See application file for complete search history.

(56) References Cited

U.S. PATENT DOCUMENTS

| | | | |
|---|---|---|---|
| 5,073,913 A * | 12/1991 | Martin | 378/34 |
| 6,635,882 B1 | 10/2003 | Pavlovic et al. | |
| 7,262,424 B2 * | 8/2007 | Moriyama et al. | 250/492.3 |
| 7,939,809 B2 * | 5/2011 | Balakin | 250/396 R |
| 2008/0067401 A1 | 3/2008 | Harada | |
| 2011/0108737 A1 * | 5/2011 | Pu et al. | 250/398 |
| 2011/0121195 A1 * | 5/2011 | Harada et al. | 250/396 ML |

FOREIGN PATENT DOCUMENTS

| | | |
|---|---|---|
| DE | 2029005 | 12/1971 |
| EP | 4359200 | 12/1992 |

(Continued)

OTHER PUBLICATIONS

Harald Paganetti et al, "Proton Therapy", Massachusetts General Hospital, Harvard Medical School, 30 Fruit Street, Boston, MA 02114, XP001249047, Oct. 1, 2005, pp. 345-363.

(Continued)

*Primary Examiner* — Nikita Wells
(74) *Attorney, Agent, or Firm* — Buchanan Ingersoll & Rooney PC

(57) ABSTRACT

There is obtained a particle beam therapy system in which the beam size is reduced. There are provided an accelerator 14 that accelerates a charged particle beam; an irradiation apparatus that has a beam scanning apparatus 5a, 5b for performing scanning with the charged particle beam and irradiates the charged particle beam onto an irradiation subject; and a beam transport apparatus 15 that has a duct for ensuring a vacuum region or gas region that continues from the accelerator 14 to a beam outlet window 7 disposed at a more downstream position than the beam scanning apparatus 5a, 5b, and that transports the charged particle beam exiting from the accelerator 14 to the irradiation apparatus.

17 Claims, 8 Drawing Sheets

FOREIGN PATENT DOCUMENTS

| | | |
|---|---|---|
| EP | 1584353 A1 | 10/2005 |
| EP | 2189184 A1 | 5/2010 |
| JP | 2001-000562 A | 1/2001 |
| JP | 2001-095932 A | 4/2001 |
| JP | 2001-178834 A | 7/2001 |
| JP | 2001-210498 A | 8/2001 |
| JP | 2002-536084 A | 10/2002 |
| JP | 2005-334383 A | 12/2005 |
| JP | 2007-229025 A | 9/2007 |
| JP | 2007-268035 A | 10/2007 |
| JP | 2008-022991 A | 2/2008 |
| JP | 2008-272139 A | 11/2008 |
| WO | 2007060242 A1 | 5/2007 |

OTHER PUBLICATIONS

European Search Report in corresponding EP Application No. 12160784, dated May 24, 2012, 7 pps.

* cited by examiner 1, 4b, 6b: VACUUM DUCT  3b: 1ST BEAM POSITION MONITOR
5a, 5b: BEAM SCANNING APPARATUS
7: BEAM OUTLET WINDOW  8: DOSE MONITOR
9: 2ND BEAM POSITION MONITOR
12: DEFLECTION ELECTROMAGNET
14: ACCELERATOR  15: BEAM TRANSPORT APPARATUS
20: DUCT EXTENSION/CONTRACTION MEANS
21: DRIVING MEANS 1, 4b, 6b: VACUUM DUCT
7: BEAM OUTLET WINDOW
8: DOSE MONITOR
9: 2ND BEAM POSITION MONITOR
20: DUCT EXTENSION/CONTRACTION MEANS
21: DRIVING MEANS
30: X-RAY SOURCE
31: IMAGE PICKUP TUBE 1: VACUUM DUCT   3a: 1ST BEAM POSITION MONITOR
5a, 5b: BEAM SCANNING APPARATUS
7: BEAM OUTLET WINDOW   9: 2ND BEAM POSITION MONITOR
21: DRIVING MEANS 1, 4a, 6a: VACUUM DUCT   2a, 2b: ISOLATION WINDOW
3a: 1ST BEAM POSITION MONITOR
5a, 5b: BEAM SCANNING APPARATUS
7: BEAM OUTLET WINDOW   9: 2ND BEAM POSITION MONITOR

PARTICLE BEAM THERAPY SYSTEM

TECHNICAL FIELD

The present invention relates to a particle beam therapy system utilized in cancer treatment or the like and particularly to a particle beam therapy system that realizes scanning irradiation.

BACKGROUND ART

The irradiation method of a particle beam therapy system is roughly divided into a broad irradiation method where beams are concurrently irradiated onto the whole diseased site of a patient as an irradiation subject and a scanning irradiation method where a diseased site is scanned with a beam. The scanning irradiation method includes a spot-scanning method, a raster-scanning method, and the like; herein, these methods will collectively be referred to as a scanning irradiation method. In order to realize the scanning irradiation method, apparatuses and control methods suitable for its irradiation method are required. The front end portion from which a charged particle beam is actually irradiated also needs to be contrived in order to realize the scanning irradiation method. The front end portion from which a charged particle beam is irradiated is referred to as an irradiation system, an irradiation field forming apparatus, an irradiation head, an irradiation nozzle, or the like; however, herein, the front end portion will be referred to as an irradiation apparatus.

In the scanning irradiation apparatus utilized in a conventional particle beam therapy system, in order to raise the accuracy of an irradiation position when the diseased site of a patient is irradiated, there has been proposed a configuration where a vacuum region or a region of gas such as helium, which is lighter than air, is ensured so that scattering of a beam is suppressed and hence the beam size is reduced (e.g., refer to Patent Document 1). The portion where a vacuum region or a gas region is ensured is referred to as a chamber (such as a beam transport chamber or a gas chamber) or a duct (such as a vacuum duct); however, it can be understood that the chamber and the duct are substantially the same. Accordingly, the foregoing portion will be referred to as a duct herein. A portion, in the duct, through which a charged particle beam passes is referred to as a window. The window is referred to as an isolation window (isolation membrane) or a beam outlet window depending on a patent document; however, herein, the most downstream window in the orbit of a charged particle beam will be referred to as a beam outlet window.

The scanning irradiation apparatus in a conventional particle beam therapy system will be explained with reference to FIG. 7. The scanning irradiation apparatus is configured with a vacuum duct 1 for ensuring a vacuum region; a window (beam outlet window) 7, in the duct 1, through which a charged particle beam passes; beam scanning apparatuses 5a and 5b for performing scanning with a charged particle beam; beam position monitors 3a and 9 for measuring the position of a charged particle beam; and a dose monitor 8 for measuring a beam dose.

Next, the operation of the scanning irradiation apparatus in a conventional particle beam therapy system will be explained. A charged particle beam accelerated by an accelerator passes through a beam transport apparatus and then is introduced into the vacuum duct 1 (in the case of FIG. 7, from the upper part to the lower part of the drawing). The charged particle beam passes through the window 7 of the vacuum duct 1 and then exits into the air; the first beam position monitor 3a confirms the beam irradiation position. At a further downstream position, the irradiation direction of the charged particle beam is controlled by the beam scanning apparatuses 5a and 5b formed of a scanning electromagnet or the like. The charged particle beam is irradiated in such a way as to follow the center line (dashed line) drawn in FIG. 7 and adjusted in such a way as to ultimately head for an isocenter (irradiation reference point) 11 when the beam scanning apparatuses 5a and 5b do not perform any control.

Usually, one of the beam scanning apparatuses 5a and 5b performs scanning in the X axis direction, and the other performs scanning in the Y axis direction. The dose of the charged particle beam is measured by the dose monitor 8 disposed at a further downstream position; the position of the beam is confirmed again by the second beam position monitor 9 disposed at a still further downstream position. The charged particle beam is finally irradiated onto the disease site of a patient as an irradiation subject. As illustrated in FIG. 7, some of the dose monitors 8 and the second beam position monitors 9 can be moved in the beam axis direction by a driving device 21 in accordance with the position and the size of the diseased site of a patient 10b as an irradiation subject. Additionally, as illustrated in FIG. 8, it is conceivable that, in order to ensure as much vacuum region as possible in a region where a charged particle beam passes, vacuum ducts 4a and 6a are additionally provided in the irradiation apparatus in a conventional particle beam therapy system.

It is conceivable that a conventional scanning irradiation apparatus is utilized and as illustrated in FIG. 8, a vacuum region or a region of gas such as helium that is lighter than air is ensured so that there is reduced beam scattering caused by air within that region. However, there has been a problem that because beam scattering caused by air is merely one of conditions that determine the size of a beam, the scanning irradiation apparatus illustrated in FIG. 8 cannot realize a small beam size that is required to perform a practical scanning irradiation. Hereinafter, further explanation will be made.

FIG. 9 is a schematic diagram for explaining the relationship between the scattering angle and the beam spot diameter. When hitting on some obstacle, a beam advancing straight is scattered and propagates with some spread. The foregoing spread is referred to as a scattering angle and expressed by $\theta$ (radian) in FIG. 9. The beam spot diameter at a position that is r (distance) apart from the obstacle is approximately $r\theta$, as illustrated in FIG. 9. In a conventional scanning irradiation apparatus, the window 7 and the first beam position monitor 3a that are disposed at a more upstream position than the scanning electromagnet correspond to the obstacles. In other words, a charged particle beam scatters at the position of the window 7 and propagates with a spread thereafter.

In the conventional technology illustrated in FIG. 7 or FIG. 8, there has been a problem that because the obstacle that causes the scattering of a beam is located far from the isocenter as an irradiation point, i.e., because the distance r in the schematic diagram in FIG. 9 is long, the beam spot diameter becomes large and hence there is not obtained a beam size small enough to be applied to practical scanning irradiation. As illustrated in FIG. 8, it is conceivable that, in order to ensure as much vacuum region as possible in a region where a charged particle beam passes, vacuum ducts 4a and 6a are additionally provided in the irradiation apparatus in a conventional particle beam therapy system. The foregoing configuration can certainly reduce beam scattering caused by air. However, this configuration does not make the position of the window 2a where a beam firstly scatters closer to the irradiation subject; therefore, it does not solve the problem completely. Additionally, the number of windows through which a charged particle beam passes becomes three (the isolation windows 2a and 2b and the beam outlet window 7), i.e., the number of windows increases, which has been a cause that makes the beam size large.

Another problem posed in the case where the vacuum region is merely added as illustrated in FIG. 8 will be explained with reference to FIG. 8. The size of the place where the diseased site of a patient as an irradiation subject is located is not always the same. For example, with regard to the cross section of the place where the diseased site of a patient as an irradiation subject is located, it should be considered that, as illustrated in FIG. 8, the size of the cross section differs depending on the patient, for example a patient 10a (type 1) or a patient 10b (type 2). Compared with the case of the patient 10a (type 1), in the case of the patient 10b (type 2), the air gap, i.e., the distance of the air path through which a charged particle beam passes becomes long.

Originally, this air gap is unnecessary; as explained with reference to the schematic diagram in FIG. 9, the distance r between the obstacle and the irradiation point should be as short as possible. There has been a problem that, even though the distance between the irradiation point and an obstacle, such as the dose monitor 8 or the second beam position monitor 9, which causes the scattering of a beam should be as short as possible, the air gap cannot be shorten in the configuration illustrated in FIG. 8 due to the system's functional restrictions.

Patent Document 1: Japanese Patent Application Laid-Open No. 2007-268035

Patent Document 2: Japanese Patent Application Laid-Open No. 2007-229025

DISCLOSURE OF THE INVENTION

Problems to be Solved by the Invention

The present invention has been implemented in order to solve the foregoing problems; the objective thereof is to obtain a particle beam therapy system in which the beam size is reduced.

Means for Solving the Problems

A particle beam therapy system according to the present invention is provided with an accelerator that accelerates a charged particle beam; an irradiation apparatus that has a beam scanning apparatus for performing scanning with the charged particle beam and a first duct in which a beam outlet window is provided at a more downstream position than the beam scanning apparatus, and that irradiates the charged particle beam onto an irradiation subject through the inside of the first duct; and a beam transport apparatus (15) that has a second duct (1) and transports, through the inside of the second duct (1), the charged particle beam exiting from the accelerator (14) to the irradiation apparatus. The particle beam therapy system according to the present invention is characterized in that a vacuum region inside the first duct and a vacuum region inside the second duct communicate with each other.

Advantage of the Invention

In the particle beam therapy system according to the present invention, a window to be disposed at a more upstream position than the scanning electromagnet is removed, and the vacuum region inside the first duct in which the beam outlet window is provided at a more downstream position than the beam scanning apparatus and the vacuum region inside the second duct of the beam transport apparatus communicate with each other, so that the number of obstacles that cause a charged particle beam to scatter is minimized; and by disposing an obstacle that causes beam scattering as downstream as possible, there can be obtained a particle beam therapy system in which the beam size is reduced.

BEST MODE FOR CARRYING OUT THE INVENTION

At first, there will be explained which factor determines the size of a beam that is irradiated onto the diseased site of a patient as an irradiation subject. A charged particle beam accelerated by an accelerator passes through a beam transport apparatus and is introduced into a duct of an irradiation apparatus. In the duct, the irradiation direction of the charged particle beam is controlled by two pairs of scanning electromagnets arranged outside the duct, in such a way as to head for the irradiation position. The charged particle beam whose direction has been controlled passes through a beam outlet window, propagates in the air, goes into the patient body, and is irradiated onto a diseased site of a cancer or the like, which is the irradiation subject.

Figure 9:
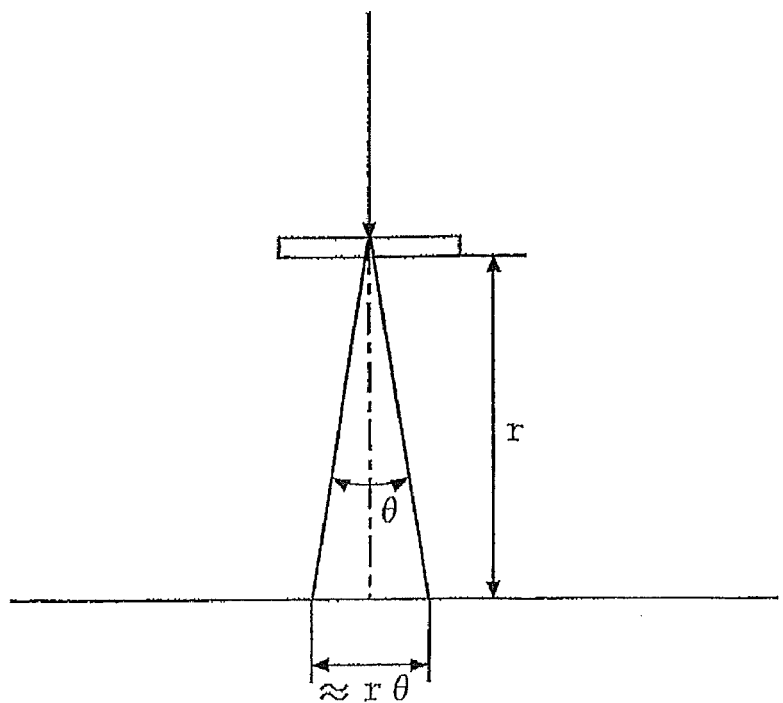
FIG. 9 is a schematic diagram for representing the relationship between the scattering angle and the beam spot diameter.

The beam size of a charged particle beam is determined by the material and the distance of a propagation path. More specifically, the level of beam scattering is determined by a medium (a vacuum) inside the duct, the length of an in-duct beam path, the material and the thickness of the beam outlet window, and the distance between the beam outlet window and an irradiation subject, whereby the beam size is determined. FIG. 9 is a schematic diagram for representing the relationship between the scattering angle and the beam spot diameter.

A characteristic of the present invention is that, in order to reduce the beam size, the vacuum region inside the first duct in which the beam outlet window is provided at a more downstream position than the beam scanning apparatus and the vacuum region inside the second duct of the beam transport apparatus communicate with each other. Furthermore, in Embodiments, various kinds of configurations described below are adopted in order to reduce the beam size.

(1) The upstream first beam position monitor is disposed in the first duct. As a result, the isolation windows at before and after the first beam position monitor are removed, so that beam scattering at the isolation window portions can be suppressed.

(2) There is provided a mechanism with which, inside the first duct, the first beam position monitor in the first duct can be evacuated from the orbit of a charged particle beam. As a result, the first beam position monitor, at an upstream position, which can be an obstacle that causes beam scattering can be evacuated from the orbit of a charged particle beam while an actual therapy is performed, so that beam scattering at this position can be eliminated.

(3) In the first duct, there are provided a duct extension/contraction means for extending or contacting the duct in the beam axis and a driving means for driving the duct extension/contraction means. As a result, the duct can be disposed as close to the irradiation subject as possible in accordance with respective cases with the different shapes of irradiation subjects; therefore, the distance of the air gap (a path through which a beam propagates in the air) can be shortened, whereby the distance r, which is an element that enlarges the beam spot diameter, can be shortened.

Because, by extending or contracting the duct in the beam axis, the duct is located close to a patient as an irradiation subject, it is instantly noticeable to a doctor or a patient where a particle beam is irradiated; therefore, the doctor or the patient can obtain the feeling of security. Moreover, some particle beam therapy systems are rotating irradiation types in which the irradiation apparatus is mounted in a rotating gantry in order to freely vary the irradiation direction up to 360°; because, while the irradiation direction is varied, the duct can be kept away from the patient, there can be avoided a risk where the irradiation apparatus hits the patient or other apparatuses.

(4) The beam outlet window is formed of aluminum. As a result, beam scattering at the beam outlet window is suppressed, and hence the beam size can be reduced.

Embodiment 1

Figure 1:
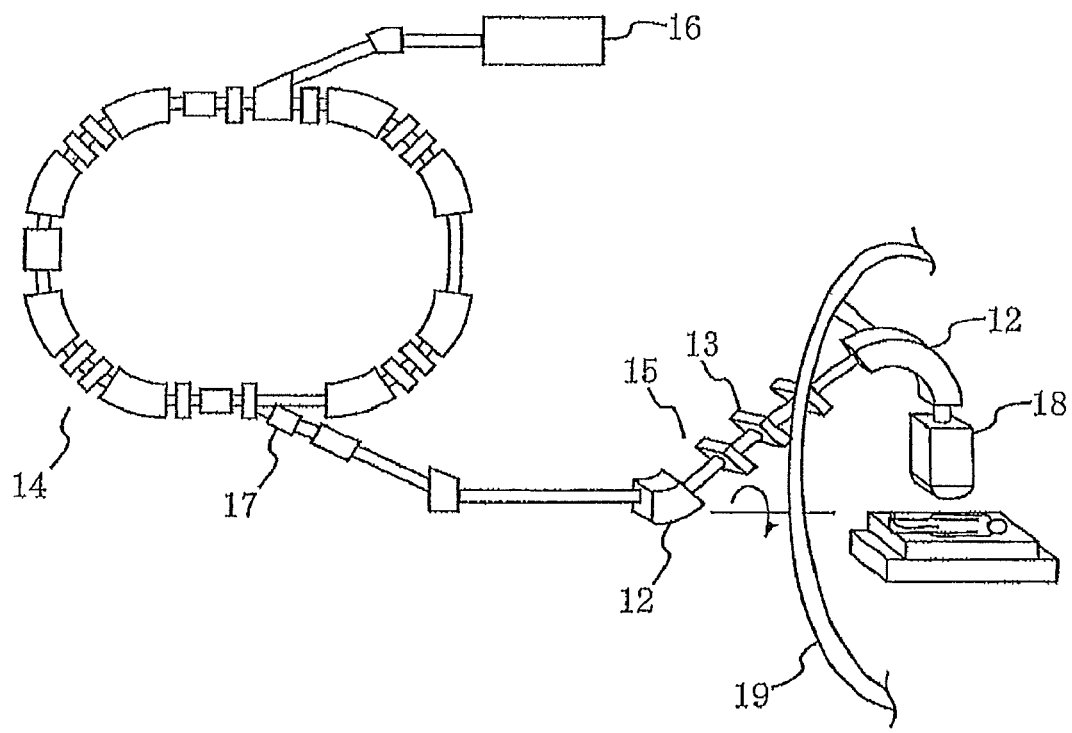
FIG. 1 is a schematic overall configuration diagram illustrating a particle beam therapy system according to Embodiment 1 of the present invention.
Figure 2:
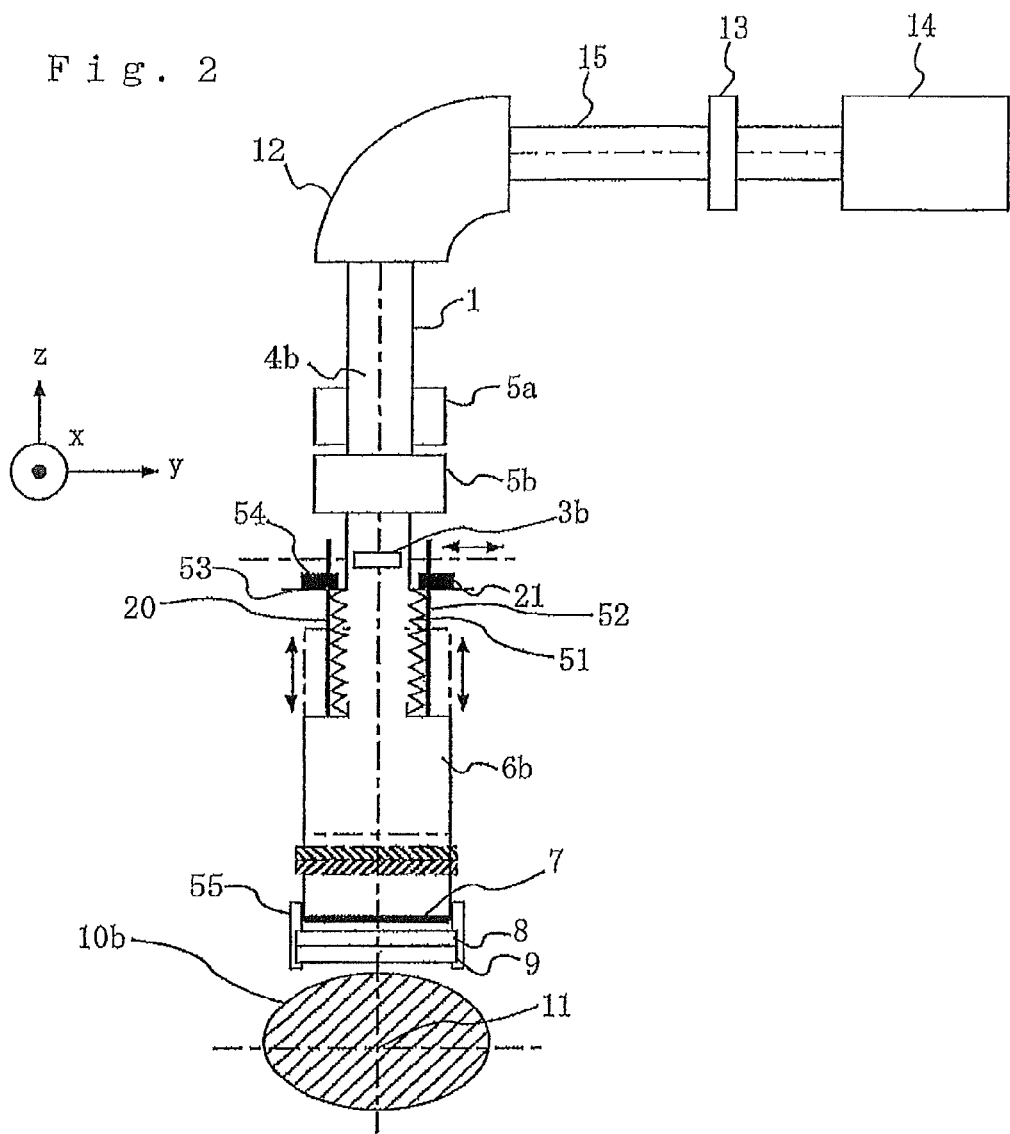
FIG. 2 is a configuration diagram illustrating a particle beam therapy system according to Embodiment 1 of the present invention.

FIG. 1 is a schematic overall configuration diagram illustrating a particle beam therapy system according to Embodiment 1 of the present invention. FIG. 2 is a configuration diagram illustrating a particle beam therapy system according to Embodiment 1. In FIG. 1, a charged particle beam that has been produced in a prestage accelerator 16 and accelerated in the prestage is injected into an accelerator (synchrotron) 14, accelerated to the point where it obtains required energy, exits to a beam transport apparatus 15 through an exit deflector 17, reaches an irradiation apparatus, and then it is irradiated onto an irradiation subject. The beam transport apparatus 15 has a focusing electromagnet 13 and a deflection electromagnet 12. Part of the beam transport apparatus 15 and the irradiation apparatus 18 are mounted on a rotating gantry 19, and the irradiation direction of the irradiation apparatus 18 can be varied through the rotation (indicated by the arrow in FIG. 1) of the rotating gantry 19.

In FIG. 2, the particle beam therapy system is configured with a beam transport apparatus 15 that has the accelerator 14, the focusing electromagnet 13, and the deflection electromagnet 12 and transports a charged particle beam, which exits from the accelerator 14, within the duct; ducts 4b and 6b that ensure a vacuum region starting from the accelerator 14 and communicate with each other; beam scanning apparatuses 5a and 5b that perform scanning with a charged particle beam; a first beam position monitor 3b that measures the position of a charged particle beam; a beam outlet window 7 through which a charged particle beam is taken out; a dose monitor 8 that measures a beam dose; a second beam position monitor 9; and a duct extension/contraction means 20 and a driving means 21 that extend and contract the duct. Characters x, y, and z denote the x direction, the y direction, and the z direction, respectively. The same reference marks in the figures indicate the same or equivalent constituent elements.

Next, the operation will be explained. The particle beam therapy system according to Embodiment 1 has four characteristics. The first characteristic of the present invention is that the vacuum region in the duct of the beam transport apparatus is extended to (communicates with) the beam outlet window disposed at a more downstream position than the beam scanning apparatus. That is to say, a duct 1 (a second duct) provided in the beam transport apparatus communicates with the ducts 4b and 6b (a first duct) provided in the irradiation apparatus, so that the vacuum region or gas region in the duct of the beam transport apparatus communicates with the beam outlet window disposed at a more downstream position than the beam scanning apparatus. Accordingly, as illustrated in FIG. 2, the number of obstacles that cause scattering of a charged particle beam is minimized, and the beam outlet window 7 that unavoidably becomes an obstacle because of its structure and through which a beam passes is disposed at a more downstream position than the beam scanning apparatus 5. As described above, by disposing an obstacle that causes beam scattering as downstream as possible, the distance r represented by the schematic diagram in FIG. 9 can be shortened; therefore, the spot size of a charged particle beam can be suppressed to be small.

Figure 8:
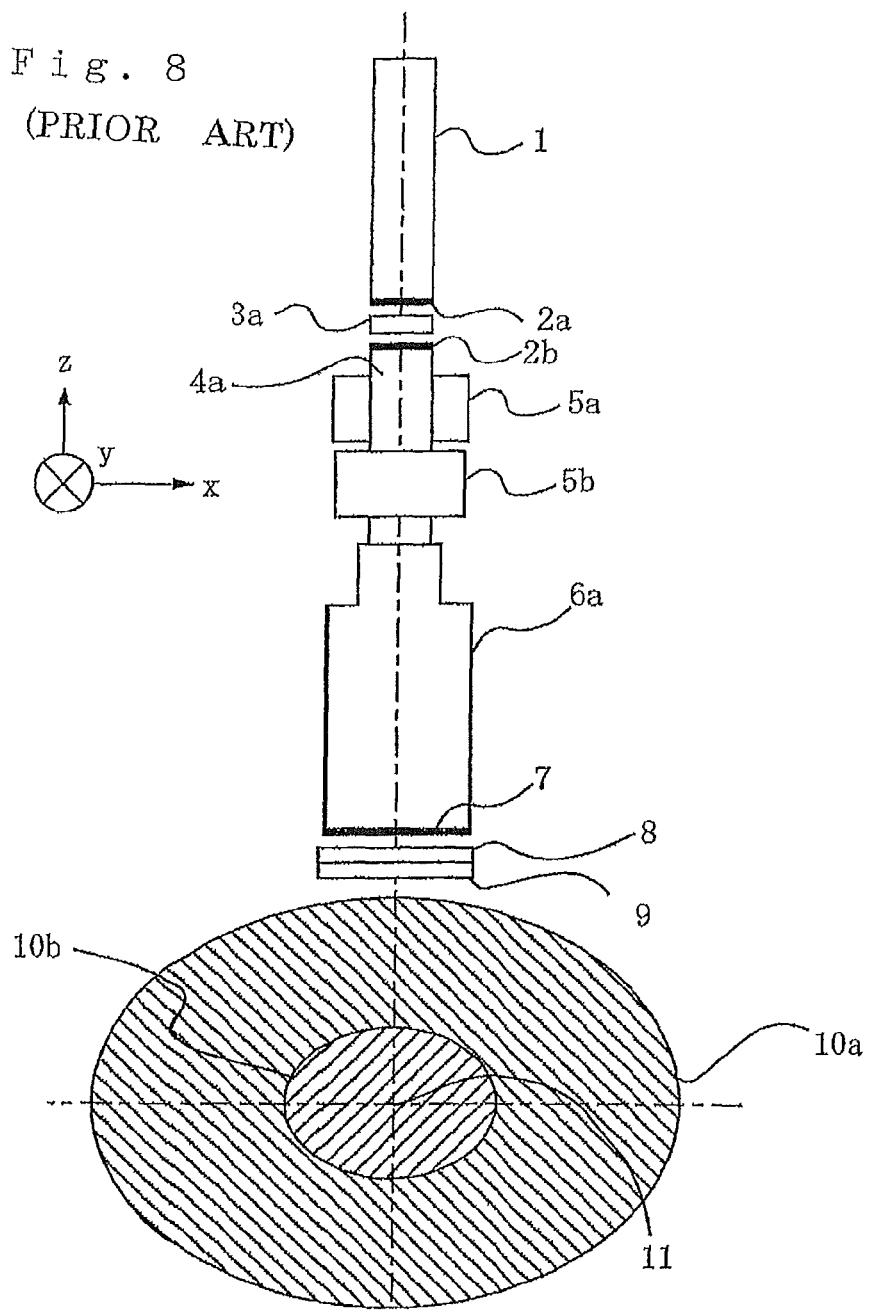
FIG. 8 is a configuration diagram illustrating another scanning irradiation apparatus in a conventional particle beam therapy system.

If it is the only requirement to be realized "that the beam outlet window 7 is disposed at a more downstream position than the beam scanning apparatuses 5a and 5b", the configuration as illustrated in FIG. 8 is conceivable. This is based on an idea of adding the combination of ducts 4a and 6a, both ends of each of which are formed of a window to a scanning irradiation apparatus according to a conventional technology, in order to increase the vacuum region out of the regions through which a charged particle beam passes. It is true that the foregoing configuration can reduce beam scattering caused by air, because air per se is also an obstacle that causes beam to scatter. However, this configuration cannot shorten the distance between the irradiation subject and the isolation windows 2a and 2b that firstly cause beam scattering; therefore, it has been difficult to suppress the spot size of a charged particle beam to be small (the scattering caused by the window is more dominant than the scattering caused by air).

The beam outlet window is disposed at a more downstream position than the beam scanning apparatus, and at the position where the beam scanning apparatus is disposed, there is ensured a vacuum region that communicates with the beam outlet window, so that the beam scattering at this portion can be reduced. In many cases, a beam scanning apparatus is formed of an electromagnet having an opening at a portion thereof through which a beam passes; by reducing the beam scattering at the position where the beam scanning apparatus is disposed, the foregoing opening can also be diminished; therefore, there is demonstrated an advantage that the beam scanning apparatus can also be downsized.

The second characteristic of the particle beam therapy system according to Embodiment 1 is that the first beam position monitor 3b that is disposed at an upstream position can be evacuated from the orbit of a charged particle beam in the duct 4b. The first beam position monitor may be disposed either at an upstream position or at a downstream position with respect to the beam scanning apparatuses 5a and 5b. FIG. 2 illustrates a case where the first beam position monitor is disposed at a downstream position with respect to the beam scanning apparatuses 5a and 5b. The first beam position monitor 3b disposed at an upstream position and the second beam position monitor 9 disposed at a downstream position are necessary in order to confirm the position of an irradiated beam; however, it is not required to always utilize the two beam position monitors 3b and 9 concurrently. That is to say, there exists an option in which the first beam position monitor 3b at an upstream position is utilized for conducting maintenance or utilized at a time before and after treatment, but not utilized during treatment irradiation. Thus, as illustrated in FIG. 2, the first beam position monitor 3b is configured in such a way that it can be evacuated from the beam orbit, as may be necessary.

Figure 3:
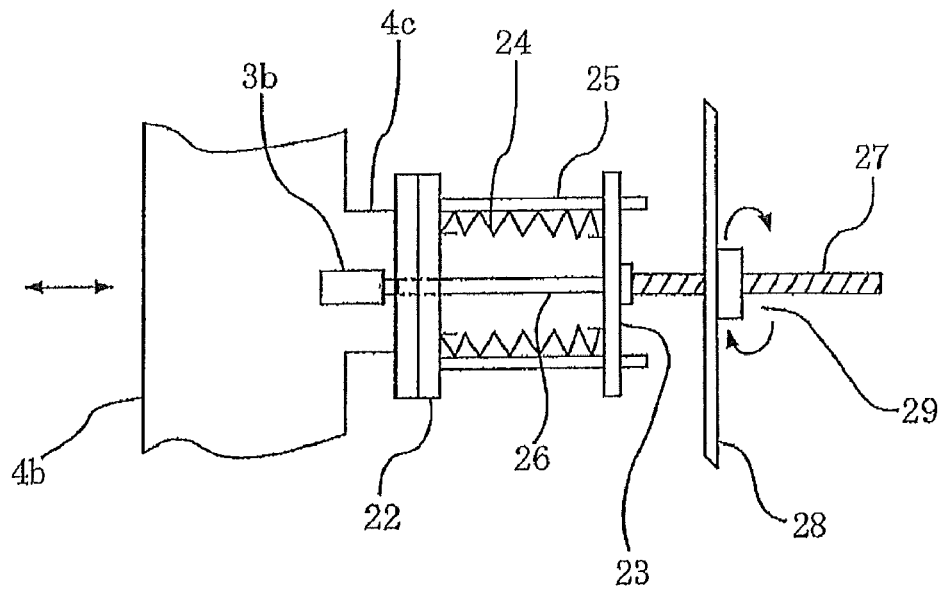
FIG. 3 is a configuration diagram illustrating an evacuation mechanism, according to Embodiment 1 of the present invention, for evacuating a beam position monitor from a beam orbit.

FIG. 3 is a configuration diagram illustrating an evacuation mechanism, according to Embodiment 1, for evacuating a beam position monitor from the beam orbit. FIG. 3 illustrates an example of the evacuation mechanism for the beam position monitor. An evacuation duct 4c is provided in the duct 4b. Reference numerals 22 and 23 denote a ring-shaped flange and an end plate, respectively; a bellows 24 is sealed and bonded between the flange 22 and the end plate 23 in such a way as to prevent the external air from entering. Reference numeral 25 denotes a guide rod that is inserted into a through-hole of the end plate 23 and guides the end plate to move back and forth. To the end plate 23, there is fixed a shaft 26 that supports the beam position monitor 3b in the duct 4c. The shaft 26 penetrates the ring-shaped flange 22. A threaded operation shaft 27 is fixed to the end plate 23 at the external air side; by rotating a nut 29, which is supported by a supporting plate 28, by means of a motor or the like, the operation shaft 27 is made to move back and forth, so that the beam position monitor 3b is made to move back and forth by the intermediary of the end plate 23 and the shaft 26. As a result, it is made possible to set the beam position monitor 3b on the beam orbit or to evacuate the beam position monitor 3b from the beam orbit.

The third characteristic of the particle beam therapy system according to Embodiment 1 is that there are provided the duct extension/contraction means 20 for extending or contacting the duct in the beam axis and the driving means 21 for driving the duct extension/contraction means. In FIG. 2, the duct extension/contraction means 20 is inserted between the duct 4b and the duct 6b, and the driving means 21 drives the duct extension/contraction means 20. Because, as described above, the duct extension/contraction means 20 and the driving means 21 are provided, any unnecessary air gap can be suppressed by extending the duct toward the patient 10b, even in the case where the air gap for the patient 10b (type 2) is enlarged with the configuration in FIG. 8 where a vacuum duct is added to a conventional technology; therefore, the beam size can be reduced.

In FIG. 2, there is provided a bellows 51 airtightly bonded between the duct 4b and the duct 6b so as to shut out the external air. Reference numeral 52 denotes a threaded operation shaft; one end thereof is fixed to the duct 6b, and the other thereof penetrates a supporting plate 53 at the duct 4b side. Reference numeral 54 denotes a nut into which the operation shaft 52 is screwed and that is held by the supporting plate 53; by rotating the nut 54 through the driving means 21, the bellows 52 is extended or contracted, and hence the duct 6b is extended or contracted with respect to the duct 4b; then, the duct can be extended or contracted in the beam axis. It is true that air is also an obstacle that causes a charged particle beam to scatter; however, the scattering caused by the window is more dominant than the scattering caused by air; suppressing the air gap reinforces the effect of shortening the distance between the irradiation subject and the beam outlet window 7. Accordingly, the beam outlet window 7 is disposed in the vicinity of the patient as an irradiation subject.

The fourth characteristic of the particle beam therapy system according to Embodiment 1 is that there is mounted a holding member for moving, in conjunction with the movement of the duct in the beam axis, the dose monitor 8 and the beam position monitor 9 provided in the vicinity of the beam outlet window 7 and at a more downstream position than the beam outlet window 7. In FIG. 2, at the front end portion of the duct 6b, the dose monitor 8 and the beam position monitor 9 are held by a holding member 55. As a result, the dose monitor 8 and the beam position monitor 9 move in conjunction with the movement (extension and contraction) of the duct in the beam axis; thus, there can be avoided a trouble that the dose monitor 8 and the beam position monitor 9 make contact with the patient 10 or an apparatus.

As Embodiment 1, there has been described a particle beam therapy system that has the first characteristic through the fourth characteristic; however, it is not required that the particle beam therapy system satisfies all of the first characteristic through the fourth characteristic. For example, even a particle beam therapy system having only the first characteristic can demonstrate the effect of suppressing the beam size to be small.

Embodiment 2

Figure 4:
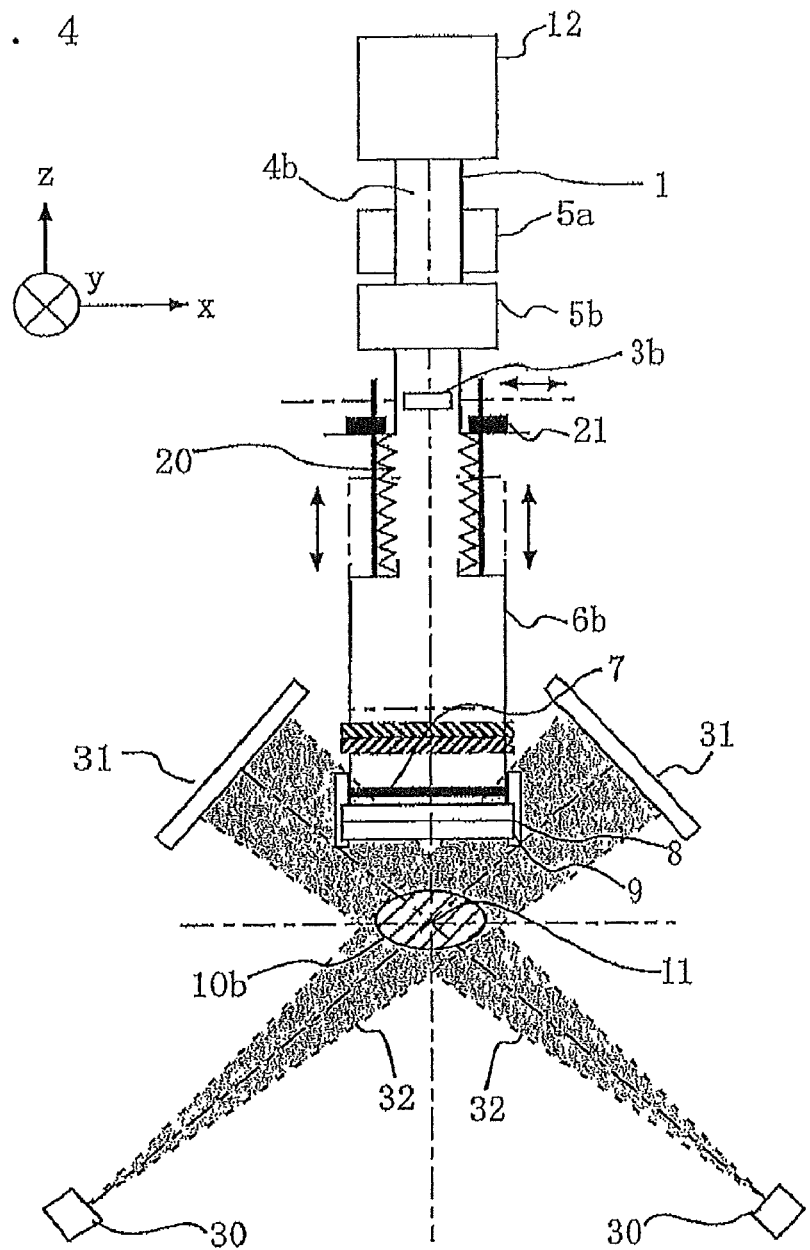
FIG. 4 is a configuration diagram illustrating a particle beam therapy system according to Embodiment 2 of the present invention.

FIG. 4 is a configuration diagram illustrating a particle beam therapy system according to Embodiment 2. In general, in a particle beam therapy system utilized in cancer treatment or the like, there is utilized an X-ray image pickup apparatus or the like for determining the accurate position of an irradiation subject, because the irradiation subject is a cancer or the like that exists in a human body. In this case, in order to determine the position of an irradiation subject, 3-dimension positional information is required; therefore, normally, two X-ray image pickup apparatuses are utilized and arranged in such a way that the image pickup directions thereof are perpendicular to each other. The X-ray image pickup apparatus is configured with an X-ray source for generating an X ray and an image pickup tube for picking up a projected X ray. The particle beam therapy system according to Embodiment 2 is provided with two X-ray image pickup apparatuses that each includes an X-ray source 30 and an image pickup tube 31; as illustrated in FIG. 4, the X-ray image pickup apparatuses each including the X-ray source and the image pickup tube that face each other are arranged in such a way that the respective image-pickup directions thereof are different from the beam axis direction of a charged particle beam. In addition, reference numeral 32 denotes an X-ray passage area.

Figure 7:
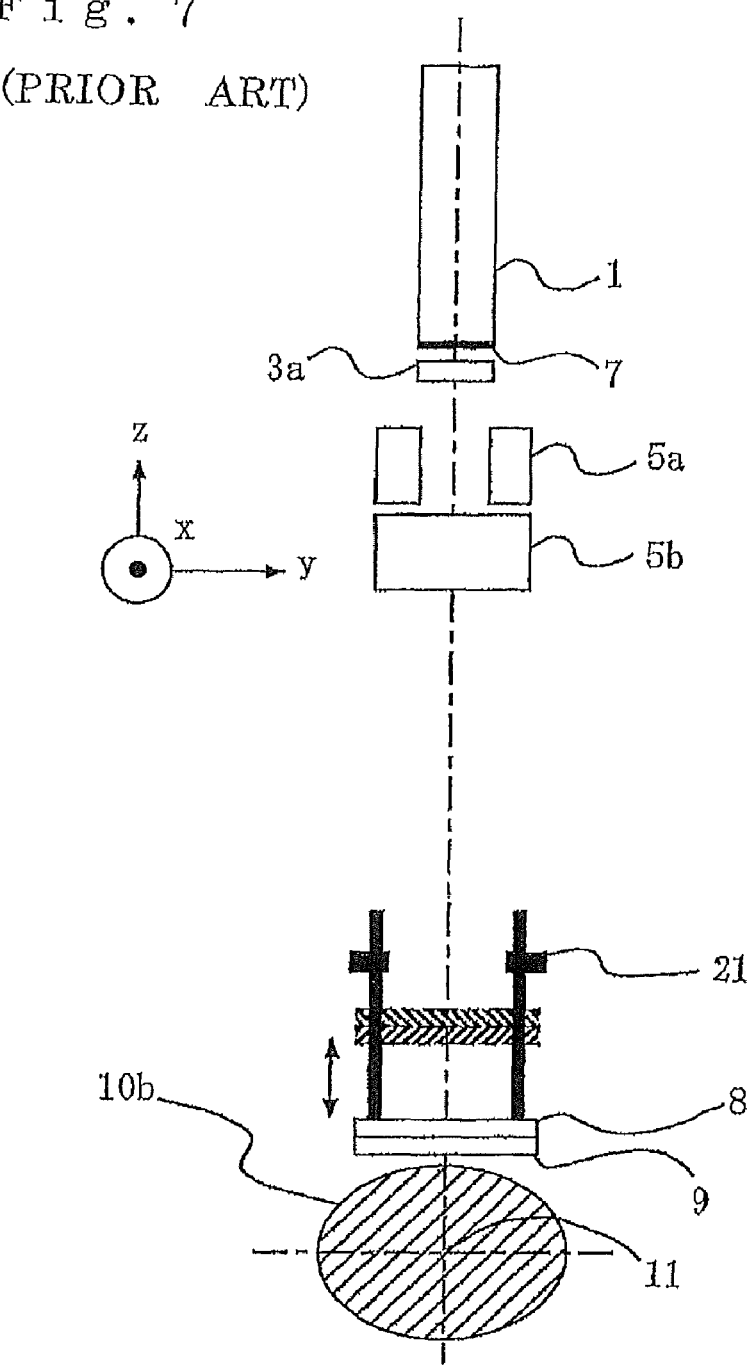
FIG. 7 is a configuration diagram illustrating a scanning irradiation apparatus in a conventional particle beam therapy system.

Compared with the conventional particle beam therapy system (in FIG. 7), the duct in the particle beam therapy system according to Embodiment 2 is extended to the vicinity of the isocenter 11 as an irradiation reference point. Accordingly, compared with the conventional particle beam therapy system, more attention must be paid to the interference between the duct 6b and the image pickup tube 31; however, as illustrated in FIG. 4, by arranging the image pickup directions of the X-ray image pickup apparatuses in such a way as to be different from the beam axis direction (i.e., the extension/contraction direction of the duct), the interference can be avoided. With regard to a particle beam therapy system utilized in cancer treatment or the like, in many cases, a rotating irradiation type utilizing a rotating gantry is adopted in order to realize 360-degree irradiation direction; it should be understood that the configuration described in Embodiment 2 may be applied to a rotating-radiation-type particle beam therapy system. In this case, the irradiation apparatus and the X-ray image pickup apparatuses are mounted on the rotating gantry and can freely be rotated while the positional relationship among the irradiation apparatus and the X-ray image pickup apparatuses are kept; therefore, arbitrary-angle X-ray image pickup is possible, and it goes without saying that vertical-direction and horizontal-direction image pickup are possible.

Embodiment 3

As illustrated in the schematic diagram of FIG. 9, when hitting an obstacle, a charged particle beam scatters. Therefore, in order to reduce the beam spot size as much as possible, it is required, ideally, that any obstacle that causes scattering is eliminated. However, there exists an element, as the beam outlet window 7, that is structurally indispensable but becomes an obstacle. The beam outlet window 7 is an indispensable member to be situated between the air and the vacuum region. With regard to an element that is structurally indispensable but becomes an obstacle that causes scattering, it is an effective contrivance that, as described in Embodiment 1, the element is disposed as downstream as possible so that the distance r illustrated in FIG. 9 is shortened as much as possible.

Considering this problem from another point of view, even in the case where an obstacle is disposed still at the same position, reducing the scattering angle can suppress the beam spot size to be small. The scattering angle changes depending on the material and the thickness of an obstacle that causes scattering. As far as the material is concerned, the younger the atomic number thereof is, the smaller the scattering angle is. As far as the thickness is concerned, the smaller the thickness thereof is, the smaller the scattering angle is.

Accordingly, in the particle beam therapy system according to Embodiment 3, the beam outlet window 7 is made of aluminum having a thickness of approximately 0.8 mm, in consideration of the radiation hardness, the strength, and the scattering angle thereof. Metal is hard against radiations; among metals, aluminum has younger atomic number (the atomic number: 13). As discussed above, by strictly selecting the material and the thickness of the beam outlet window 7, the scattering angle at the beam outlet window 7 is prevented from becoming unnecessarily large, whereby the beam spot size can be suppressed to be small. Although not illustrated, in the case where, as the material of the beam outlet window 7, a material obtained by evaporating a thin aluminum film over a resin such as Kapton (registered trademark) is utilized, a similar and superior effect can be demonstrated.

Embodiment 4

Figure 5:
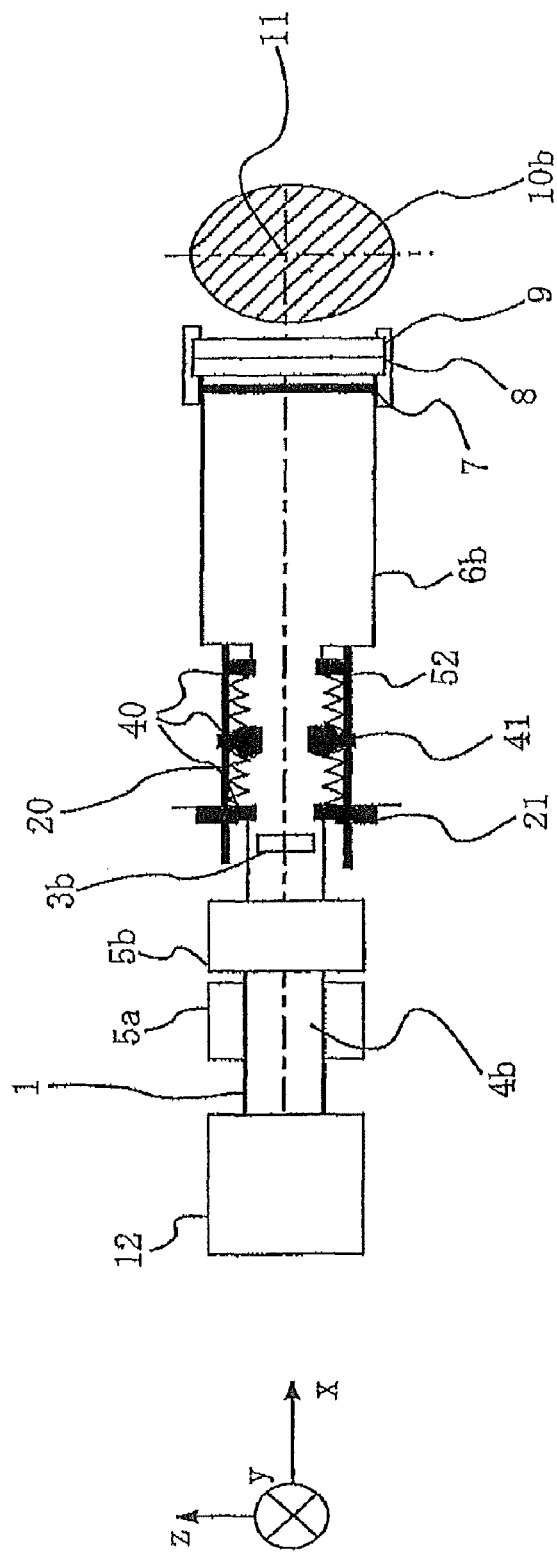
FIG. 5 is a configuration diagram illustrating a particle beam therapy system according to Embodiment 4 of the present invention.

FIG. 5 is a configuration diagram illustrating a particle beam therapy system according to Embodiment 4. There has been described an irradiation apparatus in which a charged particle beam is irradiated vertically downward; however, the actual irradiation direction varies. For example, as illustrated in FIG. 5, there also exists an irradiation apparatus in which a charged particle beam is irradiated horizontally. The characteristic of the irradiation apparatus according to Embodiment 4 is that the duct can be extended or contracted in the beam axis direction; however, this means that the irradiation apparatus becomes long, compared with a conventional irradiation apparatus. In order to maintain the long irradiation apparatus in the horizontal direction, attention must be paid to several points such as the strength and the like.

In the irradiation apparatus according to Embodiment 4, a vacuum bellows is utilized as the duct extension/contraction means 20. In particular, it is effective to use a multi-step vacuum bellows 20, because, as illustrated in FIG. 5, the vacuum bellows 20 can be prevented from slackening due to the gravity. In FIG. 5, reference numeral 40 denotes a flange; reference numeral 41 denotes a holding member for an operation shaft 52 of the flange 40. As described above, a multi-step vacuum bellows is utilized as the duct extension/contraction means 20; therefore, even in the case where the irradiation direction is the horizontal direction, irradiation with a small beam size can be realized without any problem. In addition, in the description of Embodiment 4, there has been explained a case where a multi-step vacuum bellows is utilized as the duct extension/contraction means; however, another extension/contraction means may be utilized.

Embodiment 5

Figure 6:
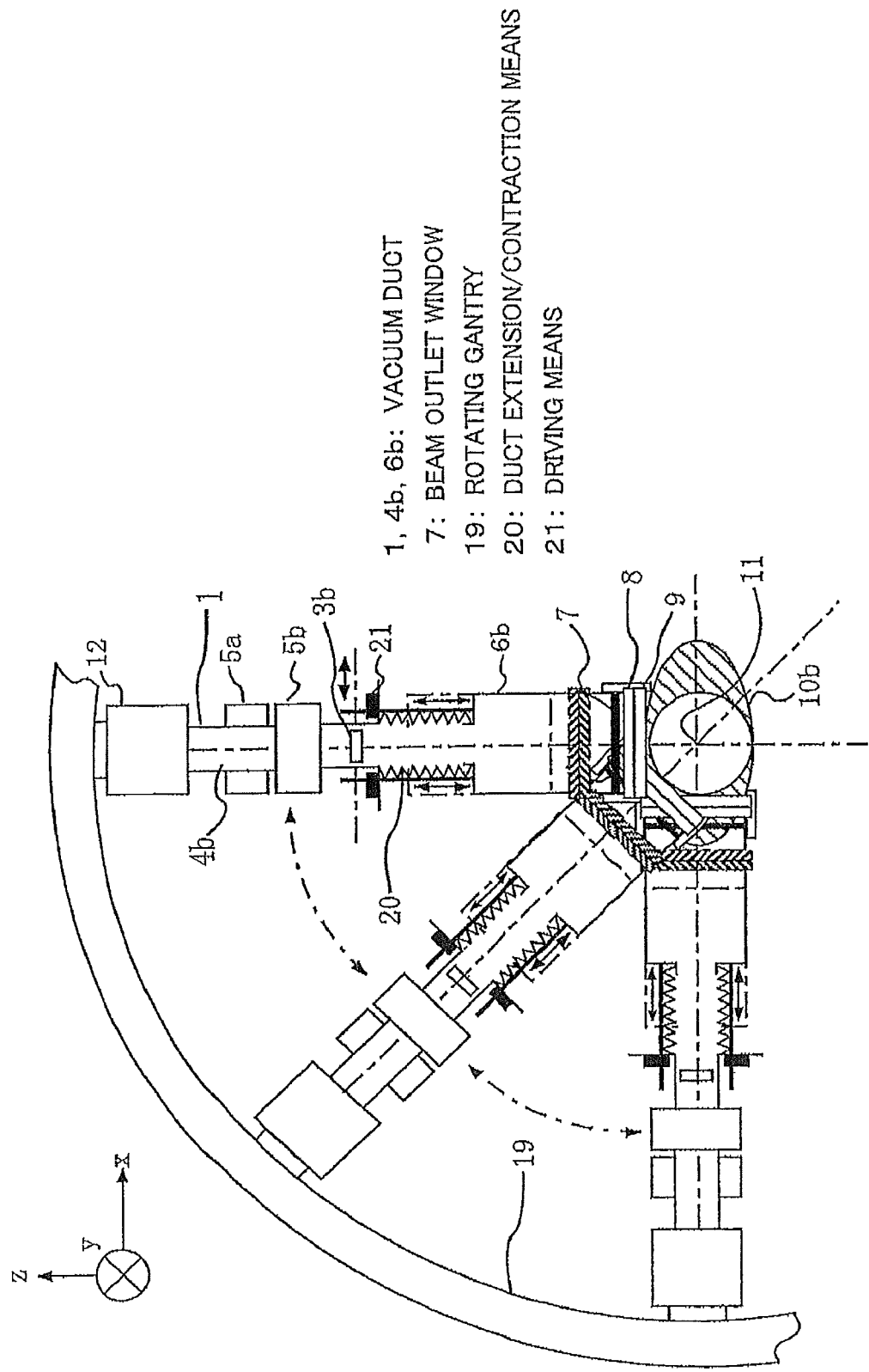
FIG. 6 is a configuration diagram illustrating a particle beam therapy system according to Embodiment 5 of the present invention.

FIG. 6 is a configuration diagram illustrating a particle beam therapy system according to Embodiment 5. Embodiment 5 is a rotating-radiation-type particle beam therapy system in which an irradiation apparatus is mounted in a rotating gantry. It goes without saying that, in each of Embodiments, irradiation can be performed by utilizing the rotating gantry. When a charged particle beam is actually irradiated, the gantry, in general, is in the stationary mode, and as described above, it is required to set the window as close to the irradiation subject as possible in order to suppress the beam size to be small. However, when the irradiation angle of the charged particle beam is changed, if the gantry is rotated with the duct kept extended, the duct and the patient as an irradiation subject may interfere with each other, as can be seen from FIG. 6.

Thus, the actual irradiation of a charged particle beam is performed with the duct extended, and the rotation of the rotating gantry for changing the irradiation angle is performed with the duct contracted. As discussed above, because the duct is made extendable and contractible, the duct and the patient as an irradiation subject do not interfere with each other even in a rotating-radiation-type particle beam therapy system having a rotating gantry; therefore, safe irradiation with beam can be performed.

Various modifications and alterations of this invention will be apparent to those skilled in the art without departing from the scope and spirit of this invention, and it should be understood that this is not limited to the illustrative embodiments set forth herein.

The invention claimed is:
1. A particle beam therapy system comprising:
   an accelerator that accelerates a charged particle beam;
   a beam scanning apparatus for performing scanning with the charged particle beam;
   a first duct that transports the charged particle beam through the inside of the beam scanning apparatus;
   an irradiation apparatus that has a second duct in which a beam outlet window is provided at a more downstream position than the beam scanning apparatus, and that irradiates the charged particle beam onto an irradiation subject through the inside of the first duct and the second duct; and a beam transport apparatus that has a third duct and transports, through the inside of the third duct, the charged particle beam exciting from the accelerator to the irradiation apparatus, wherein
the first duct and the second duct are devoid of deflection electromagnets, and
a vacuum region inside the first duct, a vacuum region inside the second duct, and a vacuum region inside the third duct communicate with one another.

2. The particle beam therapy system according to claim 1, wherein the second duct is provided with a duct extension/contraction means that enables the beam outlet window to travel in the axis direction of the charged particle beam.

3. The particle beam therapy system according to claim 2, wherein the duct extension/contraction means is formed of a bellows.

4. The particle beam therapy system according to claim 3, wherein the bellows is a multi-step type.

5. The particle beam therapy system according to claim 2, wherein the beam outlet window is disposed in the vicinity of an irradiation subject.

6. The particle beam therapy system according to claim 2, wherein there is provided an X-ray image pickup apparatus that has an X-ray source and an image pickup tube arranged in such a way as to face each other in a direction different from a traveling direction of the beam outlet window and that measures the position of the irradiation subject.

7. The particle beam therapy system according to claim 2, wherein a beam position monitor is mounted on the holding member by the intermediary of a holding member.

8. The particle beam therapy system according to claim 1, wherein there is provided a beam position monitor that is disposed in the second duct and measures the position of the charged particle beam transported in the second duct.

9. The particle beam therapy system according to claim 8, wherein the beam position monitor is disposed at a downstream position with respect to the beam scanning apparatus.

10. The particle beam therapy system according to claim 8, wherein the beam position monitor can be evacuated from the orbit of the charged particle beam in the first duct.

11. The particle beam therapy system according to claim 1, wherein the beam outlet window is made of aluminum.

12. The particle beam therapy system according to claim 1, wherein there is further provided with a rotating gantry in which part of the beam transport apparatus and the irradiation apparatus are mounted.

13. A particle beam therapy system comprising:
an accelerator that accelerates a charged particle beam;
an irradiation apparatus that has a beam scanning apparatus for performing scanning with the charged particle beam and a first duct in which a beam outlet window is provided at a more downstream position than the beam scanning apparatus, and that irradiates the charged particle beam onto an irradiation subject through the inside of the first duct;
a beam transport apparatus that has a second duct and transports, through the inside of the second duct, the charged particle beam exciting from the accelerator to the irradiation apparatus; and
a rotating gantry in which part of the beam transport apparatus and the irradiation apparatus are mounted, wherein the first duct is provided with a duct extension/contraction means that enables the beam outlet window to travel in the axis direction of the charged particle beam; and in the case where the charged particle beam is irradiated onto the irradiation subject, the duct extension/contraction means is extended, and in the case where the rotating gantry is rotated, the duct extension/contraction means is contracted.

14. The particle beam therapy system according to claim 13, wherein a vacuum region inside the first duct and a vacuum region inside the second duct communicate with each other.

15. The particle beam therapy system according to claim 13, wherein the duct extension/contraction means is formed of a bellows.

16. The particle beam therapy system according to claim 15, wherein the bellows is a multi-step type.

17. The particle beam therapy system according to claim 13, wherein the beam outlet window is disposed in the vicinity of an irradiation subject when the duct extension/contraction means is extended.

* * * * *